United States Patent [19]

Brinton

[11] Patent Number: 5,681,856
[45] Date of Patent: Oct. 28, 1997

[54] METHOD OF REDUCING FOCAL ULCERATIVE DERMATITIS (FUD) IN POULTRY

[76] Inventor: Marshall Kim Brinton, 20631 County Road 9 NE., New London, Minn. 56273

[21] Appl. No.: 603,984

[22] Filed: Feb. 20, 1996

Related U.S. Application Data

[63] Continuation-in-part of Ser. No. 355,779, Dec. 14, 1994, abandoned.

[51] Int. Cl.$^6$ .................................................. A01N 37/10
[52] U.S. Cl. .................................................. 514/568
[58] Field of Search .................................................. 514/568

[56] References Cited

U.S. PATENT DOCUMENTS 5,087,626  2/1992  Arch .
5,214,977  6/1993  Yam .

FOREIGN PATENT DOCUMENTS 278116  8/1993  Czechoslovakia .

OTHER PUBLICATIONS

Halawani, et al.—"Interrelationship Between Circulatory Testosterone Levels And The Incidence of Focal Ulcerative Dermatitis In Market Tom Turkeys", Gobbles, University of Minnesota, Oct. 1994.

Primary Examiner—Paul J. Killos
Attorney, Agent, or Firm—Haugen and Nikolai, P.A.

[57] ABSTRACT

Focal Ulcerative Dermatitis in poultry raised for consumption is prevented and treated by a method which includes the step of administering orally an effective level of aspirin over a prolonged period of time during the growth cycle of the bird.

7 Claims, No Drawings

METHOD OF REDUCING FOCAL ULCERATIVE DERMATITIS (FUD) IN POULTRY

BACKGROUND OF THE INVENTION

This application is a Continuation-in-Part of application Ser. No. 08/355,779 filed Dec. 14, 1994, abandoned.

1. Field of the Invention

The present invention is directed generally to improvements in the commercial production of poultry and, more particularly, to the use of aspirin (acetylsalicylic acid) to inhibit focal ulcerative dermatitis (FUD).

2. Related Art

Poultry production or farming on a commercial scale has become an important aspect of agriculture. Maximizing weight gain from feed, the prevention of conditions which downgrade value at market and reducing mortality in the flock are important considerations which affect the profitability of such operations. Such considerations are especially important because animals raised for consumption live under less than ideal conditions. They are exposed to crowded, less than ideal conditions simply because no one can control nature to the extent that everything is perfect and stresses are eliminated. For this reason, animals that are raised in rather large numbers under confined conditions such as, for example, poultry (turkeys and chickens) and swine must constantly deal with the stress of living with thousands of "neighbors".

One of the detrimental effects of everyday stresses which has a negative impact on healthy rapid growth in poultry is the production or synthesis of prostaglandins which result from an overproduction of the enzyme cyclo-oxygenass. Prostaglandins cause reactions in the animal which, in turn, have a generally negative effect on the well-being of the animal and its ability to thrive. Minimization of the production of prostaglandins would be generally beneficial to the well-being of animals under conditions of confinement in rather dense populations.

One widespread problem in large poultry and particularly in Tom turkeys has to do with breast blisters or focal ulcerative dermatitis (FUD). Breast blisters actually are inflammatory responses due to sustained contact with the ground or litter or when the animals rest on their keel bone. While such conditions are not serious, they do result in downgrading of the quality rating of the birds when sold for slaughter which results in a significantly lower price per pound.

In addition, increasing the efficiency of feed conversion, i.e., reducing the units of feed required per unit of weight gain by the animal being produced is a constant goal of poultry raisers. Even a seemingly small increase in efficiency results in a significant cost saving to the raiser. Of course, any safe food supplement or additive that makes the operation more efficient or profitable is desirable.

The application of certain non-steroidal anti-inflammatory drugs has been proposed to treat selected problems in raising poultry. The use of such materials to treat poultry suffering from joint infections and/or leg weakness is disclosed by Yam (U.S. Pat. No. 5,215,977). Yam indicates that such effects have been alleviated by the administration of short-term low dosages of indomethacin in drinking water or in the feed generally for seven days or less. The possible use of, inter alia, acetylsalicylic acid (aspirin) for that purpose is also disclosed although no data is presented. The reference also recognizes that indomethacin further inhibits the enzyme cyclo-oxygenase and thereby can be used to reduce prostaglandin synthesis which, in turn, reduces bone resorption.

A feed supplement or concentrated mixture for the addition of antioxidants including selenium, vitamin E, beta carotene and vitamin C is disclosed in Check Patent Document 278 116. Certain of the formulae disclosed may also contain amounts of aspirin. No benefit attributable to the aspirin is mentioned or recognized however.

The state of the art pertaining to the general knowledge surrounding the cause and treatment of focal ulcerative dermatitis (FUD) prior to the present invention was somewhat confused and an effective treatment was unknown. For example, persons well known in the field, even in 1995, speculated that testosterone levels might be the cause of FUD in market tom turkeys is evidenced by Halawani et al, "Interrelationship Between Circulatory Testosterone Levels And The Incidence of Focal Ulcerative Dermatitis In Market Tom Turkeys" Gobbles, University of Minnesota, October 1994. This further demonstrates a general lack of understanding and a clear need for the provision of a safe method for alleviating breast blisters in fowl, particularly in tom turkeys.

Accordingly, it is a primary object of the present invention to provide a method of treating poultry that particularly reduces the incidence of breast blisters or focal ulcerative dermatitis (FUD), particularly in turkeys.

A further object of the invention is to provide a method of treating poultry that uses a feed which reduces the incidence of FUD.

Another object of the invention is to provide a method of treating poultry that decreases the late mortality rate of members of production flocks.

A further object of the invention is to provide a method of treating poultry that uses a feed additive which reduces the incidences of FUD.

Another object of the invention is to provide a method of treating poultry that eases the late mortality rate of the members of production flocks.

Other objects and advantages will become manifested upon familiarity with the specification and claims herein.

SUMMARY OF THE INVENTION

According to the present invention, it has been discovered that the prolonged administration of relatively low dosages of agents that inhibit the production of prostaglandins such as non-steroidal anti-inflammatory materials, and preferably aspirin (acetylsalicylic acid) preferably beginning early in the life of the bird and extending substantially up until the time of slaughter, but for over a significant period of about eight to ten weeks or more of the life cycle of turkeys (5–6 weeks in broiler chickens) indeed imparts comprehensive benefits not heretofore recognized. Not only does the sustained low dosage of aspirin decrease the number of birds in the population which develop weak legs with the inability to properly carry the weight, particularly, of the male bird once it reaches the age of 12 to 20 weeks, the drug has decidedly unexpected additional long-term benefits when administered in low dosages over the life of the birds, including a drastic reduction in the occurrence of FUD. Lower overall mortality rates are also observed. Benefits are most pronounced if the aspirin is added to the feed over at least an eight-week period.

The method involves the administration of a prolonged low dosage of aspirin in the feed. The preferred range or dosage is between approximately 2500 and 4500 grains (0.35 to 0.65 lb) per ton (U.S.) of feed and more particularly about 3,500 grains (0.5 lb) per ton (U.S.) of feed or about 0.25 kg/metric ton of feed. This dosage range has produced a comprehensive beneficial result in the form of a greatly reduced incidence of FUD which, in turn, results in significant economic gain for the producer. This range generally corresponds to a dosage of about 3–13 mg/kg/day based on the average weight of the fowl in the flock. It must be recognized that as a food additive the actual dosage will vary with any given bird and even as that bird grows and matures. Thus, even as the relative amount of aspirin in the feed is constant, the dosage administered to an individual bird will vary according to its eating patterns during the growth cycle. A constant dosage of about 0.25 kg/metric ton of feed results in a nominal dosage of 4–10 mg/kg/day during the growth cycle of the typical male turkey. The dosage is at a maximum in young fowl (<1 lb.) which eat more in relation to their weight and progressively reduces as the bird matures.

DETAILED DESCRIPTION

The unexpected beneficial results associated with the prolonged administration of low dosage of aspirin (acetylsalicylic acid) over at least about an eight-week period during the growth cycle of large poultry produces a number of significant beneficial results, particularly the reduction of FUD. The preferred method is to administer the dosage by adding it to the poultry feed over generally what amounts to the growth life cycle of the bird. The most beneficial results are obtained in turkeys by administration for approximately eight weeks or more. A somewhat shorter period 5–6 weeks of dosage is effective in broiler chickens which are typically marketed at about 8 weeks of age. This, of course, still represents a substantial portion of the life of the fowl. The benefits primarily include a significant reduction in the occurrence of focal ulcerative dermatitis (FUD) but further with respect to quality, a significant reduction in a relative amount of condemned parts associated with the processing of the birds has also been observed. In addition, increased feed efficiency, total weight gain and reduced mortality have also been experienced.

The following examples represent studies involving rather large numbers of male turkey poults and these are intended to illustrate the advantages byway of example rather than as any limitation on the scope of the effectiveness of the treatment.

EXAMPLE 1

Approximately 15,000 male turkey poults received approximately 3,500 grains of powdered aspirin per ton of feed from 6 weeks of age until 16 weeks of age. This dosage approximates 4–10 mg/kg of body weight per day. The farms under the management of the company had previously experienced an average of approximately 20% breast blisters at processing. Also, they had experienced well over 1 per thousand daily late mortality in the last 2 to 4 weeks prior to processing at 16 to 20 weeks of age. The flock which received the aspirin was processed as "consumer toms" at approximately 16 weeks of age. The treated flock had an average breast blister prevalence of 7%, late mortality of less than 1 per thousand, and the birds weighed an average of ¾ pound over target weight. All these benefits can be directly attributed to the use of the aspirin.

EXAMPLE 2

Approximately 10,000 male turkey poults were divided into two groups of equal number (5,000) birds. One half received the same dosage as that in Example 1, from 8 weeks of age to 16 weeks of age. At processing, the group receiving the aspirin was one-half pound heavier per bird, and they graded 11% higher, and they had 2,500 fewer pounds in parts condemned; i.e., declared unusable.

EXAMPLE 3

Approximately 28,000 male turkey poults received the same dose of aspirin as those in Examples 1 and 2, from 2 weeks of age to 16 weeks of age. During the production cycle, the flock was hit with an enteric virus, followed by various sequelae which resulted in over 20% mortality. This mortality occurred after the birds were moved from the brooder barn or after they had reached 5 weeks of age. The expected feed conversion in this flock was expected to be over 3 (units of feed per unit weight gain), but the final analysis resulted in a feed conversion of only 2.58.

EXAMPLE 4

Approximately 40,000 male turkey poults received the same dose of aspirin as Examples 1, 2 and 3 from 2 weeks of age until 16 weeks of age. The mortality in the last 3 weeks, from 17 to 20 weeks of age, averaged about 1 per 2,000 per day. This represents a reduction the grower had not been able to obtain that reduced level of mortality in the past.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

For example, swine which are raised under similar conditions should also benefit from similar treatment with low dosages of non-steroidal anti-inflammatory agents. Treatment of swine should probably take place from beginning at about two weeks of age and up until within two weeks of market.

What is claimed is:

1. A method of preventing and treating focal ulcerative dermatitis in poultry raised for consumption comprising the step of administering an effective amount of aspirin in the poultry feed for a prolonged period of eight weeks or more during the growth of the poultry.

2. A method of preventing and treating focal ulcerative dermatitis (FUD) in larger poultry grown for consumption by enhancing the weight gain and preventing focal ulcerative dermatitis, comprising the step of administering a dosage of from about 3 to about 13 mg of aspirin per kg of poultry weight per day for a prolonged period of the growth cycle of the poultry.

3. The method of claim 2 wherein said prolonged period is at least eight weeks.

4. The method of claim 3 wherein the said dosage is from about 4 to about 10 mg/kg/day.

5. The method of claim 2 further comprising the step of administering said aspirin in the feed and keeping the percentage composition of the aspirin in the feed relatively constant regardless of the weight of the poultry.

6. The method of claim 3 wherein said prolonged period begins when the poultry is about two weeks of age and continues for substantially until the poultry is sold.

7. A method of preventing and treating FUD in poultry raised for consumption comprising the step of administering an effective amount of a non-steroidal anti-inflammatory agent in the poultry feed for a prolonged period of eight weeks or more during the growth of the poultry.

* * * * *